United States Patent [19]

Tan et al.

[11] Patent Number: 4,694,399

[45] Date of Patent: Sep. 15, 1987

[54] PROCESS OF IMAGE RECONSTRUCTION BY TOMODENSITOMETRY WITH IMPROVED SPATIAL RESOLUTION

[75] Inventors: Siv C. Tan, Paris; Tri H. Nguyen, Le Pre St. Gervais; Claude D. Benchimol, Paris, all of France

[73] Assignee: Thomson-CGR, Paris, France

[21] Appl. No.: 711,609

[22] Filed: Mar. 14, 1985

[30] Foreign Application Priority Data

Mar. 16, 1984 [FR] France ................. 84 04113

[51] Int. Cl.$^4$ ............................................ G06F 15/42
[52] U.S. Cl. ................................. 364/414; 358/140; 358/111
[58] Field of Search ................. 364/414; 358/140, 111

[56] References Cited

FOREIGN PATENT DOCUMENTS 2655000 6/1977 Fed. Rep. of Germany .
2708604 8/1978 Fed. Rep. of Germany .
2391696 12/1978 France .
1577046 10/1980 United Kingdom .

OTHER PUBLICATIONS

"A New Approach to Inter. In Comp. Tomography"; Journal of Comp. Ass. Tomo; R. A. Brooks, G. H. Weiss, A. J. Talbert, Nov. 1978, (pp. 577–584).

*Primary Examiner*—Jerry Smith
*Assistant Examiner*—G. Hayes
*Attorney, Agent, or Firm*—Roland Plottel

[57] ABSTRACT

In a tomodensitometric image reconstruction process the detectors 11 of the tomodensitometer are offset by $\Delta d/4$ ($\Delta d$ being the pitch of the detectors), and reconstruction is performed during one complete revolution of the detector assembly, the linear absorption values being weighed by a coefficient $\alpha$ and an equivalent number of intermediary values being produced by summing each time two successive juxtaposed real values (summation device 20) and weighing the resulting sum by a coefficient $\beta/2$ prior reconstructing the image on the basis of all these data.

2 Claims, 3 Drawing Figures

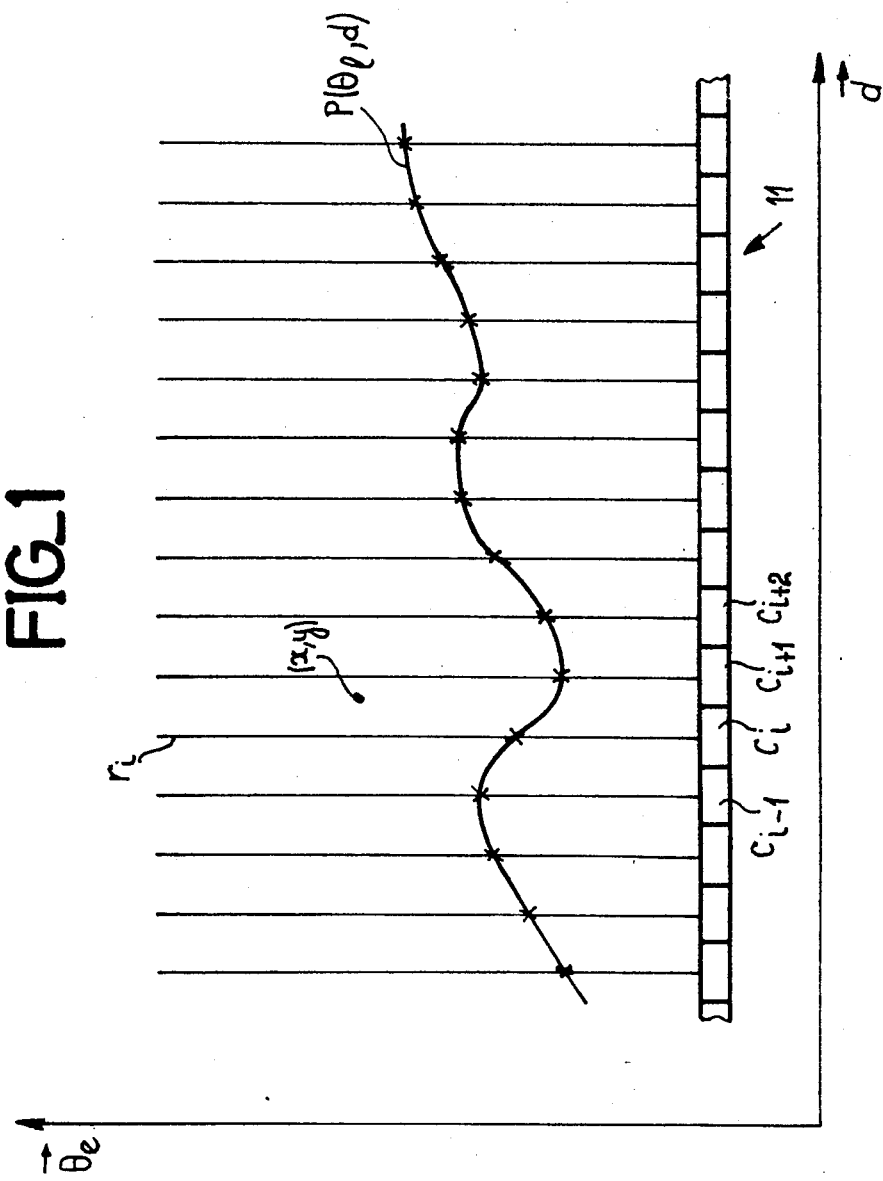

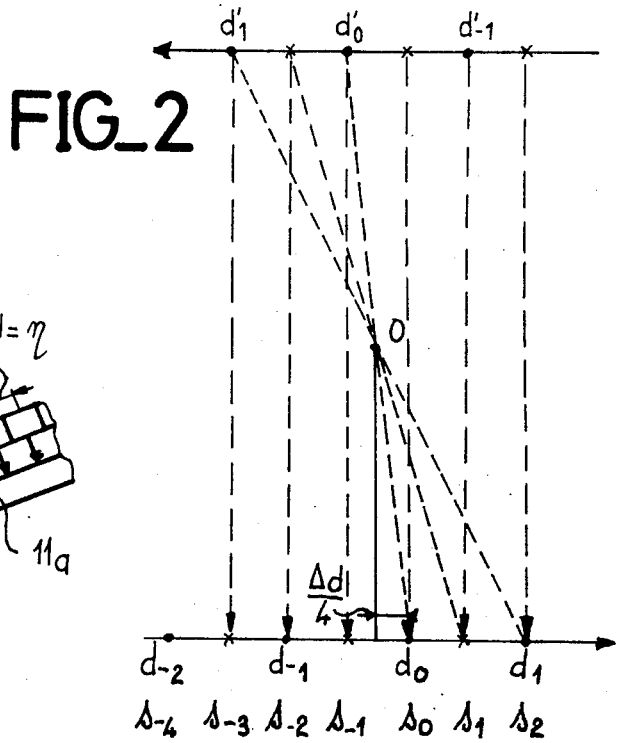
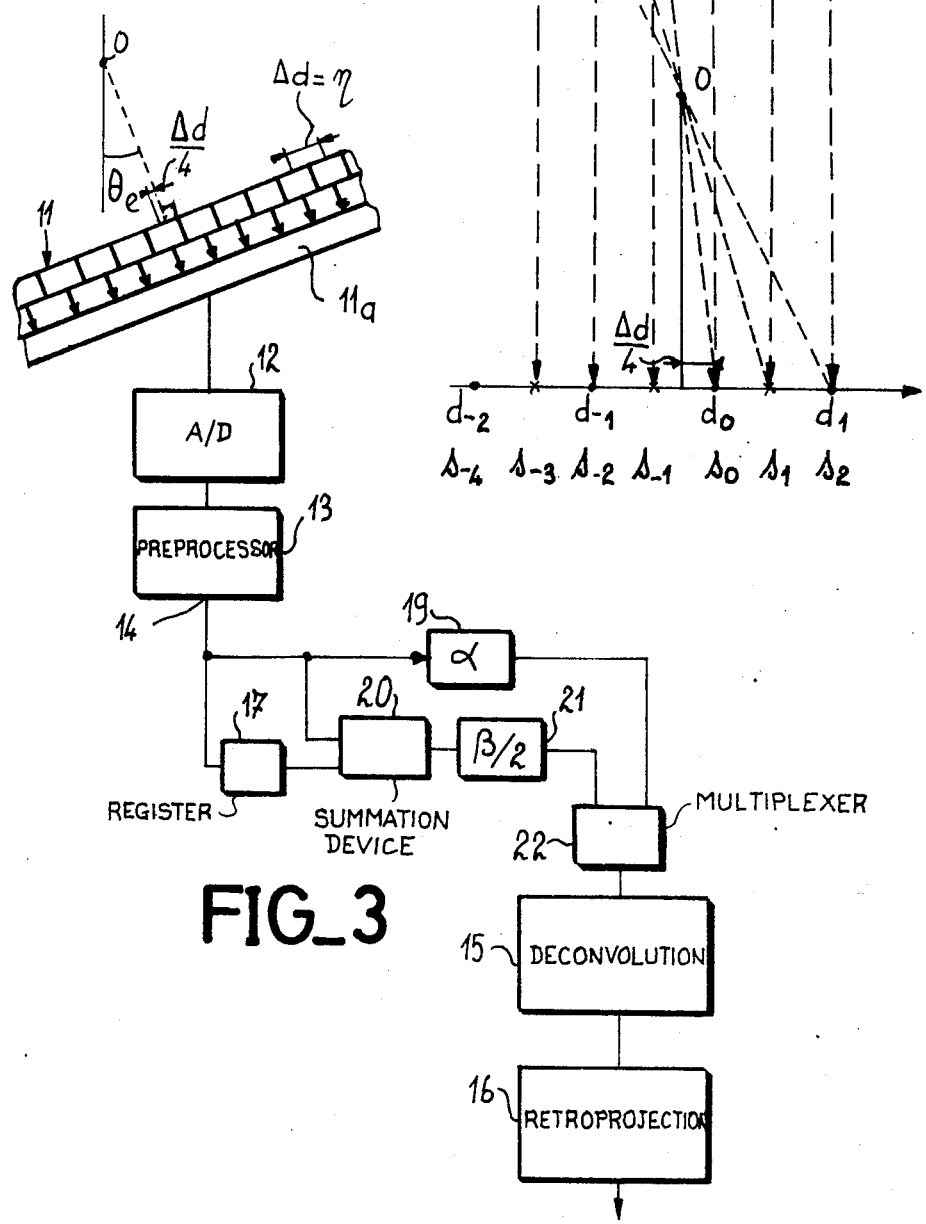
FIG_2
FIG_3

PROCESS OF IMAGE RECONSTRUCTION BY TOMODENSITOMETRY WITH IMPROVED SPATIAL RESOLUTION

FIELD OF THE INVENTION

The invention is related to a process of tomodensitometric image reconstruction, which allows to improve the spatial or tridimensional resolution of the reconstructed image without re-arrangement of the data and thus allows a rapid reconstruction of such image to be achieved.

BACKGROUND OF THE INVENTION

The development of tomodensitometric devices, or tomodensitometers, is closely related to that of the measurements achieved by the X-ray source and the detection means rotatively driven about the patient with a view to gathering the information data necessary for the reconstruction of the image. Thus several successive "generations" of tomodensitometers have been developed. The first generation, called "translation rotation generation", has used an X-ray source emitting a narrow beam toward a single detector. The source and the detector have been integral with a translationally movable assembly supported by the rotative system. For each angular position the movable assembly would be displaced transversely with respect to the section to be imaged, so as to gather a bulk of measurement values, called "view". In such system all the rays which have passed through the section to be imaged are parallel, due to the structural characteristics of the device, for a given view. The second generation has retained the principle of translation, but has used an X-ray beam in the form of a slightly flaring fan and a multi-detector comprising a small number of juxtaposed detectors. As to the tomodensitometers of the third generation, which represent the major part of the devices produced up to now, these appliances use a fan-shaped X-ray beam having a larger flaring angle, and a multidetector comprising a great number of juxtaposed detectors adapted to receive all the rays that pass through the section concerned, for every angular position adopted during the measuring operation. Thus the translational displacement at each angular position is eliminated, whereby all the data necessary for the image reconstruction can be acquired within a substantially shorter time period.

The invention allows the spatial resolution of the reconstructed image to be improved in any one of the above-mentioned tomodensitometer types.

SUMMARY DESCRIPTION OF THE INVENTION

With this object in view, the invention provides a process of tomodensitometric image reconstruction, which comprises rotating a measuring assembly including an X-ray source and detection means in the plane of a section to be imaged said detection means operating within a certain zone so as to detect the non-absorbed X-rays, taking a predetermined number of views which comprise each constant pitch samples of N values representing the linear attenuation values produced by said detection means for a given angular position of said measuring assembly, said views being taken at a constant angular pitch, and subjecting said views to deconvolution and retroprojection, said process further comprising the steps of:

setting off the centre of the detection zone by a quarter of said sampling pitch with respect to the centre of rotation of said measuring assembly;

gathering the views of an image over one complete revolution of said measuring assembly;

weighing said attenuation values for each view, by applying a first selected coefficient;

producing for each view a number of intermediary values, equivalent to the number of attenuation values, each intermediary value being obtained by adding two attenuation values corresponding to measured sampled adjacent values of said detection means and by weighing the thus obtained sum with a second selected coefficient, and applying said deconvolution and retroprojection to each group of weighed attenuation values and intermediary values corresponding to each view.

Preferably the angular pitch is a sub-multiple of one half-turn ($\pi$) of the measuring assembly. It is believed, however, that this condition is not imperative, especially when said angular pitch is small, i.e. when a great number of views are used for reconstituting the image.

As already mentioned, this definition of the invention applies to any type of tomodensitometer. More particularly, in the case of a tomodensitometer having a flared X-ray beam and a "wide-range" multidetector—which is presently the most frequently occuring case—a view is gathered by reading the multidetector for each predetermined angular position of the measuring assembly (N being the number of detectors or "channels" of said multidetector). The above-defined detection zone or range is, of course, that face of the multidetector which is directed toward the X-ray source emitting a flared or fan-shaped beam, and the offset, or shift, between the centre of said zone and the centre of rotation is an angular offset or shift.

It should be noted however that the mathematical justification herein-after of the instant novel process is rigorous only in the case of views obtained from respective families of parallel rays. Nevertheless, the process has been successfully tested by means of a "third generation" tomodensitometer with a fan-shaped X-ray beam and a "wide-range" multidetector. A very substantial improvement of the spatial resolution has been observed, especially in the central region of the image, since the rays passing through the section to be imaged may be considered as being practically parallel in the vicinity of the centre of said section. Therefore the present description will refer, as set forth herein-after, for the purpose of simplification, to a "wide-range" multidetector covering for each view the entire area of the section to be imaged, said multidetector being represented, for the present purposes, with a rectilinear structure, and considered as receiving for each "view" a family of parallel rays issuing from imaginary radiation means (not shown). Of course no existing tomodensitometer has in fact such a measuring assembly structure; it is however sufficient to know that the instant process as defined herein can be transposed and applied to a "third generation" tomodensitometer.

The invention and its features and advantages will be described in more detail herein-below, especially with reference to the appended drawing, by way of illustration, but not of limitation.

BRIEF DESCRIPTION OF THE DRAWING

In the drawing:

FIG. 1 schematically shows a multidetector irradiated by a family of parallel rays represented in a system of orthonormalized axes $(\vec{\theta_l}, \vec{d})$ characteristic of a view with the representation of the sampled absorption function p corresponding to said view;

FIG. 2 illustrates the positions of the multidetector for two offset views shifted by an amount equal to $\pi$, the locations of the centres of the real detectors being indicated by dots, while the intermediary locations corresponding to a double sampling $s_j$ are indicated by x-es;

FIG. 3 is a block diagram of a tomodensitometer incorporating the improvements according to the present invention.

DESCRIPTION OF A PREFERRED EMBODIMENT OF THE INVENTION

Known tomodensitometric reconstruction methods utilize two types of processing, i.e., on the one hand, a deconvolution, and, on the other hand, a retroprojection. The expressions associated to these two operations, as set forth herein-after, will take into account the double discretization of the system due, on the one hand, to the sampling of the absorption function, the signal being gathered from a group of juxtaposed detectors (the term "multidetector" will be utilized to designate this detector group), and on the other hand, to the angular positions $\theta_l$ of the source/detector assembly at which the different views required for the reconstruction are taken.

The deconvolution $D^\eta$ of any function $f(\theta_l, d_i)$ is conventionally represented by the expression:

$$D^\eta f(\theta_l, d_i) = \Sigma_j f(\theta_l, d_j) \cdot k(d_{i-j}) = g(\theta_l, d_i) \quad (1)$$

wherein $\eta$ represents the sampling pitch determined by detectors $c_i$, whose abscissae $d_i$ are measured on their midpoints, so that $\eta = d_i - d_{i-1}$.

It will be seen that the deconvolution is achieved view by view, i.e. with $\theta_l$ being constant; k is a function of $d_i$; it is the nucleus which characterizes the deconvolution.

Prior to undertaking the retroprojection, a supplementary operator I has to be introduced i.e.: the interpolation operator. Indeed, considering any point (x, y) of the section, to which a pixel of the image must correspond after reconstruction, it is clear that for a given angular position $\theta_l$ of the multidetector 11 (cf. FIG. 1) it is possible that no radius $r_i$ terminating at the centre of a detector $c_i$ passes through point (x, y). It is thus current practice to attribute to this point a value obtained by interpolation. It is possible, for example, to associate to this point (x, y) the radius $r_i$ which extends nearest to it in a given view (i.e. the value measured at the corresponding detector). More frequently a "barycentration" is effected between the two radii located on either side of point (x, y), or between a greater number of adjacent radii. In other terms, a mean value is calculated between the values measured at different detectors corresponding to adjacent radii, said mean value being weighed by means of a function of the difference between point (x, y) and each radius. It follows that the operator I may be represented by quite different mathematical expressions, depending on the choice made by the manufacturer of the tomodensitometer. It should be noted that the justification of the process according to the invention is based upon the supposed linearity and symmetry of the operator. The definition of the linearity of a function or an operator is well known. Furthermore, an interpolation operator is considered symmetrical if, for any pair of a discretized function and its symmetrical function to which the operator is applied, the interpolated functions of said two symmetrical functions are symmetric, too. Thus, for example, the conventional interpolation operators briefly described herein-above are linear and symmetrically.

Suppose $\tilde{g} = Ig$, wherein g is the above-defined deconvoluted function (expression (1)). The retroprojection $\{Rg^\eta\}$ (x, y), or, in other terms, R as applied to g and calculated at point (x, y) is conventionally expressed as follows:

$$\left[\begin{array}{c}\eta \\ Rg\end{array}\right](x,y) = \Sigma_l \tilde{g}(\theta_l, x \cos \theta_l + y \sin \theta_l) \quad (2)$$

It will be recalled, on the other hand, that the absorption function of the system $p(\theta, d)$ represents for each angular position $\theta_l$ of the multidetector (i.e. for each "view") the variation of the X-ray absorption in the observation area, as represented in a system of orthonormalized axes $\vec{\theta_l}, \vec{d}$ (cf. FIG. 1). Due to the construction of the multidetector, only $p(\theta_l, d_i)$ is known for each view corresponding to angle $\theta_l$, i.e. a family of samples represented by the x-values in FIG. 1.

If f were the above-defined absorption function, the retroprojection applied to the deconvoluted function f would be the reconstruction to be found. However the developments herein-after apply to any function f of $\theta_l$ and $d_i$.

Let $$\int^\eta f$$

be the global operator defined by:

$$\int^\eta f = \left\{\begin{array}{c}\eta \\ Rg\end{array}\right\}(x,y)$$

wherein g is connected to f by relation (1). This operator will be called herein-after "reconstruction operator". Furthermore, it is known that the information data required for reconstructing an image can be gathered either during a complete revolution assembly.

Let $$\int_\pi^\eta f \text{ and } \int_{2\pi}^\eta f$$

be the corresponding reconstruction operators associated to the sampling pitch $\eta$ of the multidetector. One of the conditions for carrying out the invention is that $$\Delta\theta = \theta_l - \theta_{l-1}$$

be such that $$\left|\frac{\pi}{\Delta\theta}\right| = L(\text{integer}).$$

Thus L is the number of views taken during one half-turn.

Under these conditions:

$$\int_\pi^\eta f = \sum_{l=1}^{L} \tilde{g}(\theta_l, x\cos\theta_l + y\sin\theta_l)$$

$$\int_{2\pi}^\eta f = \sum_{l=1}^{2L} \tilde{g}(\theta_l, x\cos\theta_l + y\sin\theta_l)$$

In actual practice, i.e. when f is the absorption function, it is known that:

$$\int_{2\pi}^\eta f = 2\int_\pi^\eta f$$

In other words, the image reconstructed from information data gathered during one complete revolution is the same as the image reconstructed from information data gathered during one half-turn.

The invention is aimed at exploiting this redundancy with a view to improving the spatial or tridimensional resolution of the image. For this purpose it is shown that the operators $\int_\pi$ and $\int_{2\pi}$ have the following intrinsic properties (whichever f may be):

1. $\int_\pi$ and $\int_{2\pi}$ are linear operators when I is a linear operator;
2. supposing: $\bar{f}(\theta_l, d_i) = f(\theta_{l+L}, -d_i)$ it is possible to check another property associating $\int_\pi$ and $\int_{2\pi}$:

$$\int_\pi^\eta f = \int_\pi^\eta f + \int_\pi^\eta \bar{f} = \int_\pi^\eta (f + \bar{f}) \quad (3)$$

provided that I is linear and symmetrical.

It is desired to exploit the data provided by the detectors with a sampling $\eta$ for one complete revolution (which would normally provide a reconstruction $$\int_{2\pi}^\eta ),$$

with a view to obtaining in fact an image corresponding to a reconstruction effected during one half-turn, on the basis of data obtained by a multidetector with a sampling pitch $h = \eta/2$, thus $$\int_\pi^h .$$

With this in view, consideration should be given to the abovementioned offset or shift of the multidetector centre with respect to the projection thereon of the centre of rotation O. The FIG. 2 shows that the locations $d_i'$ of the detectors, after one half turn (top of the Figure), are interlaced after projection on the bottom of the figure with the locations $d_{-i}$ and $d_{-i-1}$ of these detectors. All these locations and projections give the abscissae $s_j$ of middles of fictitious detectors usable for the double spatial resolution of the image. The abscissae $d_i$ and $d_i'$ characterize a same detector $c_i$ for two angular opposite locations of the multi-detector. The samples $s_j$ of double-sampled view are defined by the relation:

$$s_i = ih + \frac{h}{2}$$

and $$s_i - s_{i-1} = h$$

It will be also recalled that the real detectors $d_j$ are related to the pitch $\eta$ by the expression:

$$d_j = j\eta + \frac{\eta}{4}$$

consequently $$d_j = 2jh + \frac{h}{2}$$

$$d_j = s_{2j}$$

The sequence $d_j$ thus is deduced from sequence $s_i$ by gathering samples from both of them.

$p(\theta_l, d_j)$ being the absorption function samples in accordance with the pitch $\eta$ of the multidetector, it is thus the entirety of the absorption values deduced from the successive readings of the multidetector that is concerned.

Suppose the following function f representing sampling at pitch h, as defined by the double relation:

$$f(\theta_l, s_{2i}) = \alpha p(\theta_l, d_i) \quad (4a)$$

$$f(\theta_l, s_{2i+1}) = \frac{\beta}{2} p(\theta_l, d_i) + p(\theta_l, d_{i+1}) \quad (4b)$$

Introducing $\bar{f}$ in accordance with the preceding definition, it can be verified that:

$$(f + \bar{f})(\theta_l, s_i) = \alpha p(\theta_l, s_i) + \frac{\beta}{2} \{p(\theta_l, s_{i+1}) + p(\theta_l, s_{i-1})\}$$

Consequently, when supposing in a more general manner $$q(\theta, s) = \alpha p(\theta, s) + \frac{\beta}{2} \{p(\theta, s+h) + p(\theta, s-h)\} \quad (5)$$

it will be seen that $$(f + \bar{f})(\theta_l, s_i) = q(\theta_l, s_i)$$

In other words, $(f + \bar{f})(\theta_l, s_i)$ is precisely a sampled value of $q(\theta, s)$. Thus $$\int_{\pi(f + \bar{f})}^h = \int_\pi^h q$$

Now, in accordance with relation (3)

$$\int_{\pi(f+\bar{f})}^h = \int_{2\pi}^h f$$

from which follows $$\int_{2\pi}^{h} f = \int_{\pi}^{h} q$$

The envisaged object, i.e. relating $$\int_{2\pi}^{h} f \text{ to } \int_{\pi}^{h} p$$

is nearly achieved insomuch as q can be deduced from the absorption function p. Indeed, consider the Fourier transformation of relation (5) for a constant value of $\theta$ $$\hat{q}(\theta,\nu) = H(\nu) \cdot \hat{p}(\theta,\nu) \tag{6}$$

wherein $\hat{q}$ and $\hat{p}$ are respectively the Fourier transformation of q and p for a constant value of $\theta$ and wherein $$H(\nu) = a_\tau \beta \cos \pi \frac{\nu}{\nu c}$$

$\nu c = 1/2h$ is Nyquist frequency associated to the sampling with pitch h.

Thus (6) expresses that q is a "filtered version" of p. In other words, in the spatial field q is the product of the convolution of p by a nucleus $k_1$, where $k_1$ is inverse Fourier transformation of H.

Since the convolution is commutative, $$\int_{\pi}^{h} q = \int_{\pi}^{h} p$$

wherein $\lfloor$ is a homolog of $\int$ with a deconvolution nucleus k' such as $$k' = k * k_1$$

wherein * is the sign of the convolution operation.

In other words the selection of k {relation (1)}, is sufficient when the final result corresponds in fact to a deconvolution with nucleus k'. When the invention is applied to a conventional tomodensitometer with a given nucleus, it is thus sufficient to modify the deconvolution nucleus in accordance with the preceding explanation. To achieve this, a great number of possibilities are offered, since $k_1$ may also be adjusted by conveniently selecting $\alpha$ and $\beta$.

As regards the various possibilities of selection of the parameters $\alpha$ and $\beta$ it has been observed that a substantial improvement of the spatial resolution could be obtained by selecting $\alpha \neq \beta$. To resume, carrying out the process according to the invention essentially consists in modifying the values representing the absorption which are deduced from successive readings of the detection means in accordance with the double relation (4), while views are being gathered during a complete revolution.

Relation (4a) only states that each attenuation value deduced from the signal issuing from each detector $c_i$ (or for each detector position, in the case a single-detector tomodensitometer) for each view taken under an angle $\theta_l$ is weighted by a first coefficient $\alpha$, and relation (4b) states that in each view an equivalent number of intermediary values will be produced, summating up each time two attenuation values corresponding to adjacent detectors (or to successive detector positions), the resulting sum being weighed by means of a second coefficient $\beta/2$.

When selecting $\alpha = \beta = 1$, each intermediary value thus is obtained by simply calculating the mean value of two successive attenuation values.

FIG. 3 shows the main sub-assemblies of a tomodensitometer incorporating the improvements according to the present invention. The detection means are represented in this instance in the form of a multidetector 11 comprising N adjacent or juxtaposed detectors, the pitch of said detectors being $\Delta d = \eta$. For the above-indicated reasons the multidetector is represented in the form of a rectilinear casing; however it is well known that in the case of a tomodensitometer using a fan-shaped X-ray beam the casing of the multidetector may have a curvilinear shape, so that all detectors $c_i$ are arranged on a circle sector having its centre coinciding with the focus of the X-ray source (not shown). The measuring assembly, including the source and the multidetector, is rotatively driven in the plane of a section to be imaged. The centre of rotation is indicated at O. It should be recalled that the centre of the multidetector is offset, or shifted, by $\Delta d/4$ with respect to the projection of centre O on the multidetector, and that the angular pitch of the "views" gathering is such that $$\left| \frac{\pi}{\Delta \theta} \right| = L.$$

being an integer. A view is obtained in this example by reading all the detectors of multidetector 11 for a given angle $\theta_l$. Most tomodensitometers comprise adjusting means for accurately adjusting the position of the multidetector with respect to the source. In most cases, this "vernier" (or "nonius") is adjusted during the adjustment of the device so as to nullify as much as possible any offset between the multidetector and the source. The same means can be used for defining the static offset of the multidetector, which is one of the objects falling within the scope of the present invention. FIG. 3 illustrates in the form a functional block diagram the specific means provided by the invention (in accordance with one possible embodiment thereof), as well as the essential parts of the computer associated to multidetector 11. The sampled values read at the outlet terminals of the multidetector, for example by means of a circuit 11a including analog gates, are converted into digital information data through an analog/digital converter 12, and then processed in a conventional preprocessor 13 which carries out the usual logarithmic transformation and calibration operations. The thus converted information data are the linear attenuation values. To each "view" such values are associated in a number equal to that of the detectors provided in the multidetector, i.e. N values. In a manner well known per se the multidetector is read out sequentially from one end to the other, so that the attenuation values appear in succession at the output terminal 14 of the preprocessor with a view to being processed in real time in another processor of the computer which comprises essentially a section 15 adapted or programmed to perform a deconvolution, and a section 16 adapted or programmed to perform a retroprojection. According to the invention, a register 17 having its input terminal connected to output terminal 14 is interposed between preprocessor 13 and the deconvolution means.

Said output terminal 14 is also connected to a digital multiplier 19 adapted to apply the coefficient $\alpha$ and to an input terminal of a digital summation device 20 the other input terminal of which is connected to the output terminal of register 17. The output terminal of summation device 20 is connected to another digital multiplier 21 adapted to apply a coefficient $\beta/2$. The output terminals of the two multipliers 19 and 21 are connected to the two input terminals of a multiplexer 22 the output of which feeds the deconvolution section 15.

Thus due to register 17 linear attenuation values corresponding to two adjacent or juxtaposed detectors are available at every instant. The digital information data representing these attenuation values are then combined in accordance with the double relation (4$a$, 4$b$) hereinabove, by means of circuits 19, 20, 21. Thus each "view" is associated with 2N values applied to the deconvolution section. Obviously all these operations can also be performed by a simple sub-program of the computer replacing all the wired logic circuits described herein-above, between analog/digital converter 12 and deconvolution section 15.

Weighing N attenuation values with coefficient $\alpha$ produces N values. On the contrary, obtaining intermediary values from any two juxtaposed detectors for each value involves taking into account a supplementary fictitious measuring value of one side of the multidetector, which depends on the direction of offset of the multidetector, with a view to obtaining N intermediary values. In practice it is not necessary to add a supplementary detector to the measuring assembly, since it may be considered that the absorption at the edge of the section to be imaged is always nil. Consequently, for obtaining this extreme intermediary value it is sufficient to multiply by $\beta/2$ the linear absorption value corresponding to the real extreme detector.

The invention is not limited to the embodiments described and shown herein; many variants and modifications may be envisaged by those skilled in the art without departing from the spirit and scope of the invention as defined in the appended claims.

We claim:

1. A process of tomodensitometric image reconstruction, which comprises rotating a measuring assembly including an X-ray source and detection means in the plane of a section to be imaged, said detection means operating within a certain zone so as to detect the non-absorbed X-rays, taking a predetermined number of views which comprise each constant pitch samples of N values representing the linear attenuation values produced by said detection means for a given angular position of said measuring assembly, said views being taken at a constant angular pitch, and subjecting said views to deconvolution and retroprojection, said process further comprising the steps of:

setting off the centre of the detection zone by a quarter of said sampling pitch with respect to the centre of rotation of said measuring assembly;

gathering the views of an image over one complete revolution of said measuring assembly;

weighing said attenuation values for each view, by applying a first selected coefficient;

producing for each view a number of intermediary values, equivalent to the number of attenuation values, each intermediary value being obtained by adding two attenuation values corresponding to measured sampled adjacent values of said detection means and by weighing the thus obtained sum with a second selected coefficient; and applying said deconvolution and retroprojection to each group of weighed attenuation values and intermediary values corresponding to each view.

2. The image reconstruction process according to claim 1, wherein said angular pitch is a sub-multiple of one half-turn of said measuring assembly.

* * * * *